(12) United States Patent
Nozawa et al.

(10) Patent No.: US 6,599,506 B1
(45) Date of Patent: Jul. 29, 2003

(54) D-FORM POLYPEPTIDE THAT INHIBITS THE INTERACTION BETWEEN LFA-1 AND ICAM-1

(75) Inventors: Iwao Nozawa, Ibaraki (JP); Stephen Benedict, Lawrence, KS (US); Marcia Chan, Lawrence, KS (US); Teruna Siahaan, Lawrence, KS (US); Scott Tibbetts, St Louis, MO (US)

(73) Assignee: The University of Kansas, Lawrence, KS (US)

( * ) Notice: Subject to any disclaimer, the term of this patent is extended or adjusted under 35 U.S.C. 154(b) by 0 days.

(21) Appl. No.: 09/553,979

(22) Filed: Apr. 20, 2000

Related U.S. Application Data (60) Provisional application No. 60/130,432, filed on Apr. 21, 1999.

(51) Int. Cl.⁷ .......................... A61K 39/00; C07K 38/04
(52) U.S. Cl. ...................... 424/185.1; 530/328
(58) Field of Search ................... 530/300, 328; 424/185.1; 514/15

(56) References Cited

U.S. PATENT DOCUMENTS

| | | |
|---|---|---|
| 5,192,746 A | 3/1993 | Lobl et al. |
| 5,340,800 A | 8/1994 | Liu et al. |
| 5,821,329 A | 10/1998 | Lobl et al. |
| 5,843,885 A * | 12/1998 | Benedict et al. |

OTHER PUBLICATIONS

Ngo et al., in The Protein Folding Problem and Tertiary Structure Prediction, 1994, Merz et al., (ed.), Birkhauser, Boston, MA, pp. 433 and 492–495.*
Partridge, Peptide Drug Delivery to the Brain, Raven Press, New York, 1991, p. 247.*

* cited by examiner

*Primary Examiner*—Christina Chan
*Assistant Examiner*—Maher Haddad
(74) *Attorney, Agent, or Firm*—John R. Wetherell, Jr.; Pillsbury Winthrop LLP (57) ABSTRACT

Methods and compositions useful in inhibiting integrin-associated diseases are provided. The compositions contain a polypeptide having one or more D-amino acids that inhibit integrin binding to its associated binding polypeptide. The compositions include retro-inverso polypeptides.

5 Claims, 3 Drawing Sheets

SEQUENCE LISTING

```
<160> NUMBER OF SEQ ID NOS: 6

<210> SEQ ID NO 1
<211> LENGTH: 25
<212> TYPE: PRT
<213> ORGANISM: Artificial Sequence
<220> FEATURE:
<223> OTHER INFORMATION: Description of Artificial Sequence: synthetic
      peptide sequence

<400> SEQUENCE: 1

Asp Leu Ser Tyr Ser Leu Asp Asp Leu Arg Asn Val Lys Lys Leu Gly
 1               5                  10                  15

Gly Asp Leu Leu Arg Ala Leu Asn Glu
             20                  25

<210> SEQ ID NO 2
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide sequence
<220> FEATURE:
<221> NAME/KEY: MOD_RES
<222> LOCATION: (1)
<223> OTHER INFORMATION: Xaa at residue 1 is a penicillamine residue;

<400> SEQUENCE: 2

Xaa Asp Leu Arg Asn Val Lys Lys Leu Gly Gly Cys
 1               5                  10

<210> SEQ ID NO 3
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide sequence
<220> FEATURE:
<221> NAME/KEY: MOD_RES
<222> LOCATION: (1)
<223> OTHER INFORMATION: Xaa at residue 1 is a penicillamine residue

<400> SEQUENCE: 3

Xaa Asp Leu Ser Tyr Ser Leu Asp Asp Leu Arg Cys
 1               5                  10

<210> SEQ ID NO 4
<211> LENGTH: 10
```

```
<212> TYPE: PRT
<213> ORGANISM: Artificial Sequence
<220> FEATURE:
<223> OTHER INFORMATION: Description of Artificial Sequence: Synthetic
      peptide sequence
<220> FEATURE:
<221> NAME/KEY: MOD_RES
<222> LOCATION: (1)..(10)
<223> OTHER INFORMATION: Residues 1 to 10 are D-amino acids

<400> SEQUENCE: 4

Gly Gly Asp Leu Leu Arg Ala Leu Asn Glu
 1               5                  10

<210> SEQ ID NO 5
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide sequence
<220> FEATURE:
<221> NAME/KEY: MOD_RES
<222> LOCATION: (1)..(10)
<223> OTHER INFORMATION: Residues 1 to 10 are D-amino acids

<400> SEQUENCE: 5

Asp Leu Arg Asn Val Lys Lys Leu Gly Gly
 1               5                  10

<210> SEQ ID NO 6
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide sequence
<220> FEATURE:
<221> NAME/KEY: MOD_RES
<222> LOCATION: (1)..(10)
<223> OTHER INFORMATION: Residues 1 to 10 are D-amino acids

<400> SEQUENCE: 6

Asp Leu Ser Tyr Ser Leu Asp Asp Leu Arg
 1               5                  10
```

D-FORM POLYPEPTIDE THAT INHIBITS THE INTERACTION BETWEEN LFA-1 AND ICAM-1

This application claims the benefit of priority to U.S. provisional application No. 60/130,432, filed Apr. 21, 1999.

FIELD OF THE INVENTION

The present invention relates to polypeptides having D-amino acids which inhibit the binding of leukocyte function-associated antigen (LFA-1) and intracellular adhesion molecule (ICAM-1). These D-form polypeptides can be used to treat disorders such as rejection of transplanted organs, allergies, and autoimmune diseases.

BACKGROUND OF THE INVENTION

Many autoimmune diseases occur when T-cells of an organism recognize and react to "self" proteins. This recognition occurs when specific proteins on the surface of the T-cells bind to the corresponding self proteins. This type of reaction results in such autoimmune diseases as rheumatoid arthritis, insulin-dependent diabetes mellitus, multiple sclerosis, and allograft rejection.

Initiation of an immune response to an antigen involves interaction of a small subset of T-cells with the antigen, followed by activation and proliferation of those T-cell clones. Complete T-cell activation requires two signals: (1) a first signal resulting from the interaction of the T-cell receptor with an appropriate MHC-antigen complex, and (2) a second signal provided by adhesion molecules. The second signal may be provided by binding of the adhesion receptor, LFA-1 (CD11$a$ and CD18), to one of its counter-receptors such as ICAM-1 (CD54) (Staunton et al., 1990, Cell 61:243–254). If the second signal is blocked, the antigen-specific T-cells are induced to die by apoptosis or to enter a state of cellular anergy. Blockage of this interaction by monoclonal antibodies to LFA-1 and ICAM-1 results in increased survival time for mice receiving a heart allograft (Isobe et al., 1992, Science 255: I 125–1 127).

SUMMARY OF THE INVENTION

The present invention is based on the seminal finding that D-amino acid polypeptides having sequence homology with cell adhesion molecules, such as ICAM-1 or LFA-1 can inhibit interaction between a particular adhesion receptor and its counter receptor or ligand.

For example, D-amino acid polypeptides with homology to either LFA-1 or ICAM-1, can bind to either ICAM-1 or LFA-1, respectively, and these D-form polypeptides used to inhibit undesirable interaction between ICAM-1 and LFA-1.

In a first embodiment, the invention provides a polypeptide having a sequence comprising one or more D-amino acids, wherein the polypeptide is derived from an LFA-1 binding site. In a preferred embodiment the polypeptide sequence has a sequence as set forth in SEQ ID NO:6.

In another embodiment, the invention provides a polypeptide having at least one D-amino acid, wherein the polypeptide has a sequence as set forth in SEQ ID NO:6. In another aspect of this embodiment, all of the amino acids of the polypeptide are D-amino acids.

In another embodiment, a method of inhibiting the interaction of ICAM-1 and LFA-1 by contacting a sample containing ICAM-1 and LFA-1 with a polypeptide having at least one D-amino acid, and having a sequence as set forth in SEQ ID NO:6, is provided. In another aspect of this embodiment, all of the amino acids of the polypeptide are D-amino acids.

In yet another embodiment, the invention provides a method for inhibiting an integrin-associated disease by contacting a subject with an inhibiting-effective amount of a polypeptide having a sequence comprising one or more D-amino acids, wherein the polypeptide has a sequence as set forth in SEQ ID NO:6. In one aspect of this embodiment, the integrin-associated disease is selected from the group consisting an allergy, an autoimmune disease, transplant rejection, and the autoimmune disease is selected from the group consisting of rheumatoid arthritis, insulin-dependent diabetes and multiple sclerosis. The subject may be any mammal, but is preferably a human. The contacting may be done in vivo or ex vivo.

In yet a further embodiment, a therapeutic composition comprising, a polypeptide derived from an LFA-1 binding site, wherein the polypeptide has a sequence comprising one or more D-amino acids and has a sequence as set forth in SEQ ID NO:6, is provided.

The details of one or more embodiments of the invention are set forth in the accompanying figures and the description below. Other features, objects, and advantages of the invention will be apparent from the description and drawings, and from the claims.

DETAILED DESCRIPTION OF THE INVENTION

The present invention provides a polypeptide having one or more D-form amino acids wherein the polypeptide inhibits binding of an integrin to its corresponding integrin-binding protein. For example, a D-form polypeptide of the invention derived from a β-subunit of LFA-1 (CD18) prevents the interaction of LFA-1 and ICAM-1.

As used herein, "polypeptide" or "peptide" means a polymer of more than one amino acid. The polypeptide of the invention includes functional fragments thereof. By "functional fragments" or "functionally equivalent" as utilized herein, refers to a polypeptide capable of exhibiting a substantially similar in vivo or in vitro activity as a polypeptide of the present invention (i.e., SEQ ID NO:1–6) described herein, as judged by any of a number of criteria, including but not limited to antigenicity, immunogenicity, as well as biological activity. Examples of biological activity include antigenicity, ability to prevent interaction, binding ability as well as other activities associated with the activity of the polypeptide of the invention.

It is intended that a polypeptide sequence of the invention include any compound having an amino acid sequence that is functionally equivalent to the sequence of SEQ ID NO:1–6. For example, one skilled in the art will recognize that substitutions of amino acids can be made using natural amino acids which result in a conservative change, or using non-natural or synthetic amino acids that result in a polypeptide having similar or equivalent functionality. Such amino acids include lysine, homoarginine, N-methyl arginine or a mimic of these amino acids which are functionally equivalent to arginine. As used herein, "mimic" means an amino acid or analog that has a similar functional characteristic or biological activity. Such characteristics include hydrophilicity, hydrophobicity, charge, side-chains and pH. Additionally, the term "amino acid" includes, for example, naturally occurring as well as non-naturally occurring amino acids and imino acids, analogs and mimics. One skilled in the art will recognize that unless indicated otherwise both (L)-amino acids and (D)-amino acids are encompassed by the present definitions and invention. For example, it may be desirable to include one or more (D)-amino acids to increase the stability of the polypeptide.

In addition, the invention may include proteins or polypeptides that represent functionally equivalent polypeptides. Such equivalents may contain deletions, additions, or substitutions of amino acid residues within the amino acid sequence of the polypeptides of the invention, but which results in a silent change, thus producing a functionally equivalent product. Amino acid substitutions may be made on the basis of similarity in polarity, charge, solubility, hydrophobicity, hydrophilicity, and/or the amphipathic nature of the residues involved.

For example, nonpolar (hydrophobic) amino acids include alanine, leucine, isoleucine, valine, proline, phenylalanine, tryptophan, and methionine; planar neutral amino acids include glycine, serine, threonine, cysteine, tyrosine, asparagine, and glutamine; positively charged (basic) amino acids include arginine, lysine, and histidine; and negatively charged (acidic) amino acids include aspartic acid and glutamic acid.

A useful modification of a polypeptide of the invention is one that confers, for example, increased stability, or reduced antigenicity. For example, incorporation of one or more D-amino acids or substitution or deletion of lysine can increase the stability and modify a polypeptide's antigenicity. For example, the inclusion of one or more D-form amino acids in a polypeptide of the invention increases its stability. The D-amino acids confer increased stability by protecting the peptide from endoprotease degradation, as is well known in the art (Partridge, *Peptide Drug Delivery to the Brain*, Raven Press, New York, 1991, page 247). These modifications increase stability and, thus, bioavailability of peptide SEQ ID NOs:1–6, but do not affect activity in inhibiting integrin-receptor interactions.

As used herein, "retro-inverso" means an amino-carboxy inversion as well as enantiomeric change in one or more amino acids (i.e., levantory (L) to dextrorotary (D)). A polypeptide of the invention encompasses, for example, amino-carboxy inversions of the amino acid sequence, amino-carboxy inversions containing one or more D-amino acids, and non-inverted sequence containing one or more D-amino acids. Retroinverso peptidomimetics that are stable and retain bioactivity can be devised as described by Brugidou et al. (*Biochem. Biophys. Res. Comm.* 214(2): 685–693, 1995) and Chorev et al. (*Trends Biotechnol.* 13(10): 438–445, 1995). The overall structural features of the retro-inverso peptide are similar to those of the parent L-peptide. The two molecules, however, are roughly mirror images because they share inherently chiral secondary structure elements. Main-chain peptidomimetics based on peptide-bond reversal and inversion of chirality represent important structural alterations for peptides and proteins, and are highly significant for biotechnology; for example, the D-HIV-protease dimer cleaves only all-D substrate, and an all-D-hexapeptide opioid is able to produce analgesia following intraperitoneal administration (Chorev et al., *Trends Biotechnol.* 13(10): 438–445, 1995). Antigenicity and immunogenicity can be achieved by metabolically stable antigens such as all-D and retroinversoisomers of natural antigenic peptides. Several integrin and integrin-binding peptidomimetics are provided in the Examples below.

The polypeptide of the invention may be prepared by conventional automated peptide synthesis and screened for activity as described in the Examples, below, by one of ordinary skill in the art. For example, sequences or peptides can be synthesized, by an automated synthesizer. Such automated synthesizers are common in the art and include for example, Applied Biosystems, Inc. Model 431 A. For techniques in using an automated synthesizer see, Steward and Yound, In Solid Phases Peptide Synthesis, 2nd ed. Pierce Chemical Co., Rockford, Ill. (1984), which is incorporated herein by reference. The integrin-associated peptides of the invention can be produced by chemical synthesis, for example, by the solid phase peptide synthesis method of Merrifield et al. (*J. Am. Chem. Soc.* 85:2149, 1964). Standard solution methods well known in the art also can be used to synthesize a peptide useful in the invention (see, for example, Bodanszky, *Principles of Peptide Synthesis*, Springer-Verlag, Berlin, 1984; and Bodanszky, *Peptide Chemistry*, Springer-Verlag, Berlin, 1993). A newly synthesized peptide can be purified, for example, by high performance liquid chromatography (HPLC), and can be characterized using, for example, mass spectrometry, or amino acid sequence analysis. A chemically synthesized peptide may be prepared on an Applied Biosystems Model 430 peptide synthesizer using an automated solid-phase protocol provided by the manufacturer. Peptides may then be purified by high performance liquid chromatography (HPLC) on a Vydac C4 column to an extent greater than 95%. Those skilled in the art will recognize that peptides can be commercially synthesized by a variety of techniques employing either Fmoc chemistry or Boc chemistry. Similar active peptides derived from integrin or integrin-binding proteins, such as LFA-1 and ICAM-1, are also within the scope of this invention, and can also be similarly prepared and screened.

It is understood that any contact site within an integrin and its corresponding integrin-binding protein are encompassed by the present invention. For example, the contact sites within LFA-1 and ICAM-1 can be used to develop a polypeptide as described in the Examples below. Polypeptides of the invention are developed by identifying contact sites between integrin and integrin-binding proteins. Once the amino acid sequence of the contact site is identified, polypeptide sequences are provided using, for example, L-amino acids, D-amino acids or a combination of L- and D-amino acids. The polypeptide may be further assayed, if desirable, to determine its biological activity, e.g., the ability to prevent integrin-binding, using for example a mixed lymphocyte reaction, collagen induced arthritis (CIA) study or organ transplant study.

A number of methods for identifying contact sites are known to those of skill in the art. For example, three standard methods by which contact sites within proteins are identified are described herein. All three methods require that the gene encoding the protein is cloned and the sequence known. A plurality of such sequences have been reported in the art.

One method has been previously described (Stanley et al., 1994, EMBO 13:1790–1798, the teaching of which is incorporated by reference herein). In this method, a domain of the first or second protein is removed by deleting the corresponding segment from the gene encoding the protein. The altered gene is expressed in bacteria to produce an altered protein. The altered protein is then assayed for its ability to bind to the other protein. If the altered protein does not bind to the other protein, the contact site was removed. The contact site is thereby localized.

Another method is employed once a contact site has been localized as described above. This method involves site-directed mutagenesis of the gene of the protein to identify precisely which amino acids are involved in protein binding. A specific nucleotide is altered in order to change a single amino acid in the contact site. An altered protein generated in this manner is then assayed for its ability to bind to a complementary or counter protein as described above. The importance of the specific amino acid to protein binding is thereby deduced. Those skilled in the art recognize that site-directed mutagenesis is a routine and widely used technique. In fact, many site-directed mutagenesis kits are commercially available. One such kit is the "Transformer Site Directed Mutagenesis Kit" sold by Clontech Laboratories (Palo Alto, Calif.).

Still another method is the "Yeast Two-Hybrid System." This method can be performed using commercially available kits. One such kit is the "MATCHMAKER Two-Hybrid System" sold by Clontech Laboratories (Palo Alto, Calif.). In this method, a domain of the first protein is subcloned into a plasmid (Plasmid A) and is expressed in yeast as a fusion protein. This fusion protein contains a domain of a yeast transcription factor in addition to the domain of the first protein. The gene of the second protein is also subcloned into a plasmid (Plasmid B) and is also expressed in yeast as a fusion protein; in this case, the fusion protein contains a different domain of the yeast transcription factor. If the domains of the first protein and the second protein bind within the yeast cell, a functional hybrid transcription factor is formed from the transcription-factor domains encoded by Plasmids A and B. This hybrid transcription factor results in the expression of a reporter gene. Thus, expression of the reporter gene indicates that the domains of the first and second proteins contain contact sites of Proteins A and B.

The polypeptides of the invention can be assayed in any number of ways well known to those of skill in the art. For example, a mixed lymphocyte reaction (MLR) assay can be used. MLR is a good predictor of in vivo activity to aid in selection of inhibitory polypeptides. This is because the MLR measures a biological readout, namely cell interaction followed by induced proliferation. Thus, the MLR is a direct measurement of allogeneic T-cell responses. Moreover, the MLR directly models the events involved in bone marrow transplantation, and indirectly predicts the biological effectiveness of the D-amino acid polypeptides in organ transplantation and in the treatment of autoimmune diseases such as rheumatoid arthritis, insulin-dependent diabetes, and multiple sclerosis. A detailed protocol of the MLR is set forth in the Examples below.

In one embodiment of the invention, noncontiguous domains of LFA-1 and ICAM-1, which are believed to be the contact sites of the two proteins, were selected from screening. The sequences of LFA-1 and ICAM-1 are known. Polypeptides based on the sequences found in these contact sites were commercially synthesized using standard techniques. Some of the polypeptides were cyclized. MLR assays were conducted to determine whether the polypeptides consisting of D-amino acids derived from LFA-1 or ICAM-1 retain a biological function such as the ability to inhibit cell proliferation.

One such D-form polypeptide (D-LBEL, SEQ ID NO:6) was significantly effective in inhibiting T-cell proliferation in MLR assays. Those of ordinary skill in the art will understand that the results of in vitro experiments described herein are predicative of the efficacy of such D-form polypeptides in treating disease states such as rejection of transplanted organs, allergies, and autoimmune diseases.

As used herein, to "inhibit" or "inhibiting" activity is to reduce that activity a measurable amount, such as a reduction of at least 30% or more. Where there are multiple different activities that may be inhibited (for example, blocking binding of a receptor to its ligand and initiation of secondary messenger activity), the reduction of any single activity (with or without the other activities) is sufficient to fall within the scope of this definition.

The present invention provides a method for treating a subject having an integrin-associated disease. By "integrin-associated" is meant any disease that requires interaction of an integrin molecule with its ligand, for example LFA-1 interaction with ICAM-1. Such integrin-associated diseases include, for example, allergies, autoimmune diseases, allograft and transplant rejection. An example of some autoimmune diseases include, rheumatoid arthritis, insulin-dependent diabetes and multiple sclerosis. Thus, where an integrin-associated disease is associated with the interaction of an integrin and its ligand the polypeptides of the invention can modulate or inhibit the disease by affecting the interaction of the integrin with its binding protein.

The polypeptide sequences of the invention can effectively inhibit and treat integrin-associated diseases. The polypeptides of the invention can be delivered to a sample, cell, or a subject in vivo. Typically the subject is a mammal and more typically a human. Binding of the polypeptide sequence to its ligand can be used to inhibit cell binding, growth, or integrin-associated diseases. Furthermore, the polypeptide sequence can be used in combination with other agents; the combination therapy may prove more effective than either sequence or agent alone.

In order for the target cell, sample, tissue, or subject to be rendered susceptible to the polypeptide sequence in accordance with the method of the invention, the cell must be exposed to the sequence under condition that facilitate contact with the cell, tissue, or subject to be treated with the polypeptide sequence. In vitro therapy may be accomplished by a number of procedures, including, for example, simple incubation of a cell or tissue with the polypeptide sequence in a suitable nutrient medium for a period of time suitable to inhibit integrin mediated interactions.

The polypeptide sequence of the invention can be delivered alone or in conjunction with other agents such as chemotherapeutic drugs, RGD-peptides, ribozymes or anti-sense molecules. In addition, the polypeptide sequence of the invention can be delivered during, after, or as part of a surgical procedure to treat an integrin-associated disorder.

Additionally, the polypeptide sequence of the present invention may be administered ex vivo by harvesting a cell or tissue from a subject, treating the cell or tissue with the sequence, then returning the treated cell or tissue to the subject. Such treatments may prove useful in organ transplantation procedures.

Many of the methods as described herein can be performed in vivo or ex vivo. The polypeptide sequence of the invention can be administered to provide in vivo therapy to a subject having an integrin-associated disease. Such therapy can be accomplished by administering ex vivo or in vivo as the case may be, a therapeutically effective amount of D-form polypeptide sequence. The term "therapeutically effective" means that the amount of a polypeptide sequence administered in a sufficient quantity to suppress or inhibit, to some beneficial degree, integrin-mediated interactions.

The polypeptide sequence according to the present invention, including D-form polypeptides, can be administered to the subject in any acceptable manner including orally, by injection, using an implant, nasally and the like. Oral administration includes administering an polypeptide sequence of the present invention in tablets, suspension, implants, solutions, emulsions, capsules, powders, syrups, water composition, and the like. Nasal administration includes administering the composition of the present invention in sprays, solutions, and the like. Injections and implants are preferred because they permit precise control of the timing and dosage levels useful for administration, with injections being most preferred. Polypeptide sequences are can be administered parenterally.

The therapeutic agents useful in the method of the invention can be administered parenterally by injection or by gradual perfusion over time. Administration may be intravenously, intra-peritoneally, intramuscularly, subcutaneously, intra-cavity, or transdermally.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's intravenous vehicles include fluid and nutrient replenishers, electrolyte replenishers (such as those based on Ringer's dextrose), and the like. Preservatives and other additives may also be present, such as antimicrobials, antioxidants, chelating agents and inert gases and the like.

The actual dosage of a polypeptide sequence of the invention, formulation, or composition that modulates an integrin-associated disease depend on many factors, including the size and health of an individual, however, one of ordinary skill in the art can use the following teachings (Spilker B., *Guide to Clinical Studies and Developing Protocols*, Raven Press Books, Ltd., New York, 1984, pp. 7–13, 54–60; Spilker B., *Guide to Clinical Trials*, Raven Press, Ltd., New York, 1991, pp. 93–101; Craig C., and R. Stitzel, eds., *Modern Pharmacology*, d. ed., Little, Brown and Co., Boston, 1986, pp. 127–33; T. Sleight, ed., *Avery's Drug Treatment: Principles and Practice of Clinical Pharmacology and Therapeutics*, 3d ed., Williams and Wilkins, Baltimore, 1987, pp. 50–56; R. Tallarida, R. Raffa and P. McGonigle, *Principles in General Pharmacology*, Springer-Verlag, New York, 1988, pp. 18–20) to determine the appropriate dosage to administer. A polypeptide sequence of the invention may be conveniently administered in unit dosage form, and may be prepared by any of the methods well known in the pharmaceutical art, for example, as described in *Remington's Pharmaceutical Sciences* (Mack Pub. Co., Easton, Pa., 1990).

Physiologically acceptable and pharmaceutically acceptable excipients and carriers are well known to those of skill in the art. By "physiologically or pharmaceutically acceptable carrier" as used herein means any substantially non-toxic carrier for administration in which a polypeptide sequence of the invention will remain stable and bioavailable when used. For example, the polypeptide sequence of the invention can be dissolved in a liquid, dispersed, or emulsified in a medium in a conventional manner to form a liquid preparation or is mixed with a semi-solid (gel) or solid carrier to form a paste, ointment, cream, lotion or the like.

Suitable carriers include water, petroleum jelly (VASELINE®), petrolatum, mineral oil, vegetable oil, animal oil, organic and inorganic waxes, such as microcrystalline, paraffin and ozocerite wax, natural polymers, such as xanthanes, gelatin, cellulose, or gum arabic, synthetic polymers, such as discussed below, alcohols, polyols, water and the like. A water miscible carrier composition that is substantially miscible in water can be used. Such water miscible carrier composition can include those made with one or more ingredients set forth above but can also include sustained or delayed release carrier, including water containing, water dispersible or water soluble compositions, such as liposomes, microsponges, microspheres or microcapsules, aqueous base ointments, water-in-oil or oil-in-water emulsions or gels.

The carrier can comprise a sustained release or delayed release carrier. The carrier is any material capable of sustained or delayed release of the polypeptide sequence specifically directed against an integrin or integrin binding molecule to provide a more efficient administration resulting in one or more less frequent and/or decreased dosage of the polypeptide sequence, ease of handling, and extended or delayed effects. The carrier is capable of releasing the polypeptide sequence when exposed to the environment of the area for diagnosis or treatment or by diffusing or by release dependent on the degree of loading of the sequence to the carrier in order to obtain release of the polypeptide of the invention. Non-limiting examples of such carriers include liposomes, microsponges, microspheres, gene-activated matrices, as described above, or microcapsules of natural and synthetic polymers and the like. Examples of suitable carriers for sustained or delayed release in a moist environment include gelatin, gum arabic, xanthane polymers; by degree of loading include lignin polymers and the like; by oily, fatty or waxy environment include thermoplastic or flexible thermoset resin or elastomer including thermoplastic resins such as polyvinyl halides, polyvinyl esters, polyvinylidene halides and halogenated polyolefins, elastomers such as brasiliensis, polydienes, and halogenated natural and synthetic rubbers, and flexible thermoset resins such as polyurethanes, epoxy resins and the like. The sustained or delayed release carrier can be a liposome, microsponge, microsphere or gel. A pH balanced buffered aqueous solution for injection can be used. However, the preferred carrier will vary with the mode of administration. The compositions for administration usually contain from about 0.0001% to about 90% by weight of the polypeptide sequence compared to the total weight of the composition.

The following examples are set forth by way of illustration only, and are not to be taken as a limitation upon the overall scope of the invention.

EXAMPLE 1

Polypeptides were synthesized at Genosys Biotechnologies, Inc. or Multiple Peptide Systems. Peptide synthesis was generally conducted according to the standard-phase protocols employing Fmoc chemistry. Linear peptides having a penicillamine residue (Pen) in the sequence and a cysteine residue a the carboxy-terminal ends were cyclized by forming a disulfide bridge between the terminal residues by adding dropwise, a 2% aqueous potassium ferricyanide solution, to dilute peptide solutions.

Table 1, below, shows polypeptides constructs in accordance with the present invention, corresponding to the identified Sequence Identification Numbers (SEQ ID Nos).

with 3,000–5,000 rad of ionizing radiation from γ137Cs source. One hundred µl of each cell suspension were combined in each well of a 96-well plate in the absence or presence of varying concentrations of test polypeptides, as detailed below. Cell proliferation was assessed after 72 hours, by 3H-thymidine addition to each well (1 µCi/well, 67 Ci/mmol) with incubation for six hours. The cells were harvested using a PHD Cell Harvester (Cambridge Technology, Inc., Watertown, Mass.); the incorporated 3H was assessed using a liquid scintillation counter (Packard Instrument, Inc., Donner's Grove, Ill.).

TABLE 1

Polypeptides Assessed in MLR Assay

| SEQ ID | Code | Sequence | Description |
|---|---|---|---|
| No. 1 | LBE | H-DLSYSLDDLRNVKKLGGDLLRALNE-OH | L-form, linear |
| No. 2 | cLBEC | H-PenDLRNVKKLGGC-NH2 | L-form, cyclic |
| No. 3 | cLBEL | H-PenDLSYSLDDLRC-NH2 | L-form, cyclic |
| No. 4 | D-LBER | H-GGDLLRALNE-OH | D-form, linear |
| No. 5 | D-LBEC | H-DLRNVKKLGG-H | D-form, linear |
| No. 6 | D-LBEL | H-DLSYSLDDLR-OH | D-form, linear |

EXAMPLE 2

Mixed Lymphocyte Reaction (MLR) assays were performed on the polypeptides to determine whether they had a desired biological activity. MLR assay was performed using certain polypeptides in accordance with the invention, in order to demonstrate that any D-form polypeptide inhibits the biological effectiveness of the involved T cells. Table 2 demonstrates the effectiveness of the various peptides used.

Figure 1:
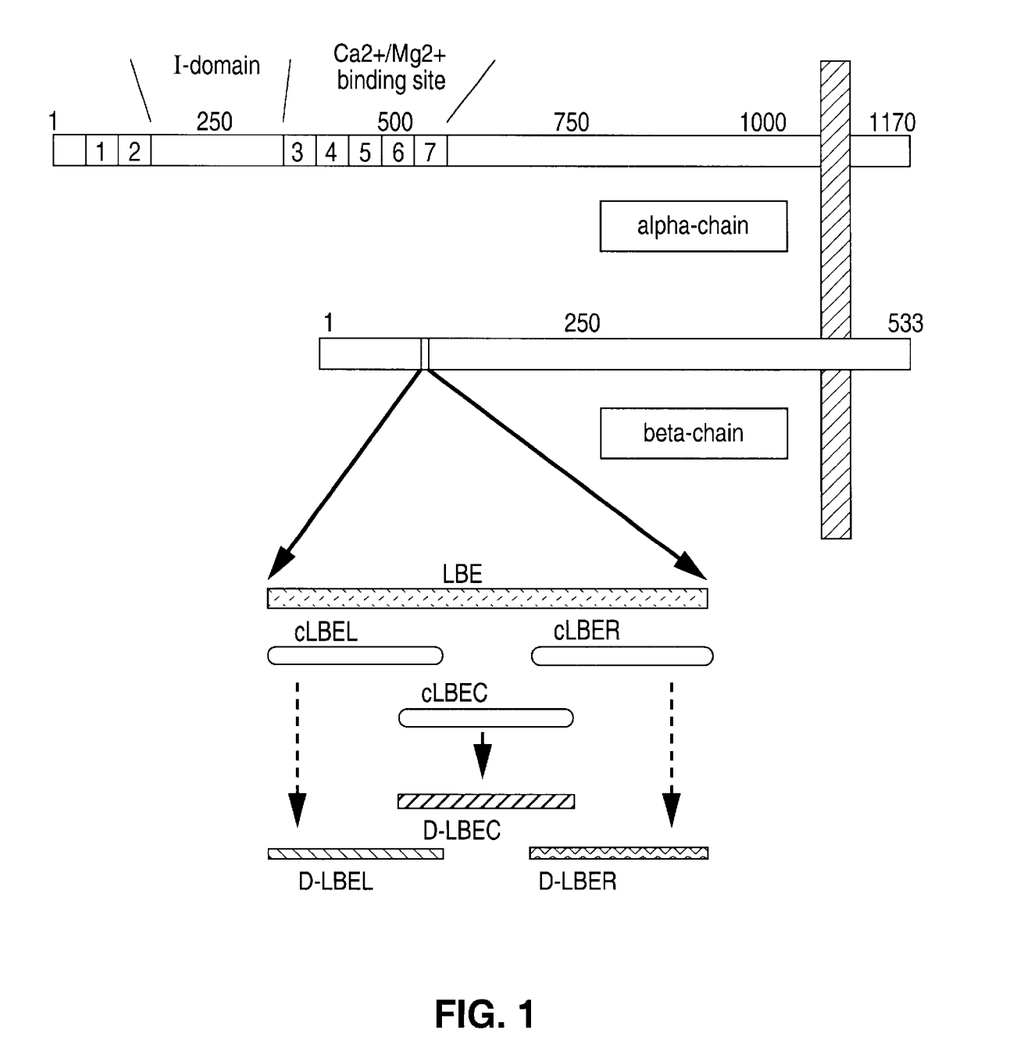
FIG. 1 is a diagram illustrating L-form polypeptides derived from a β-subunit of LFA-1 (CD18), LBE (SEQ ID NO:1), cLBEC (SEQ ID NO:2), cLBEL (SEQ ID NO:3) and D-form polypeptides, D-LBER (SEQ ID NO:4), D-LBEC (SEQ ID NO:5) and D-LBEL (SEQ ID NO:6).
Figure 2:
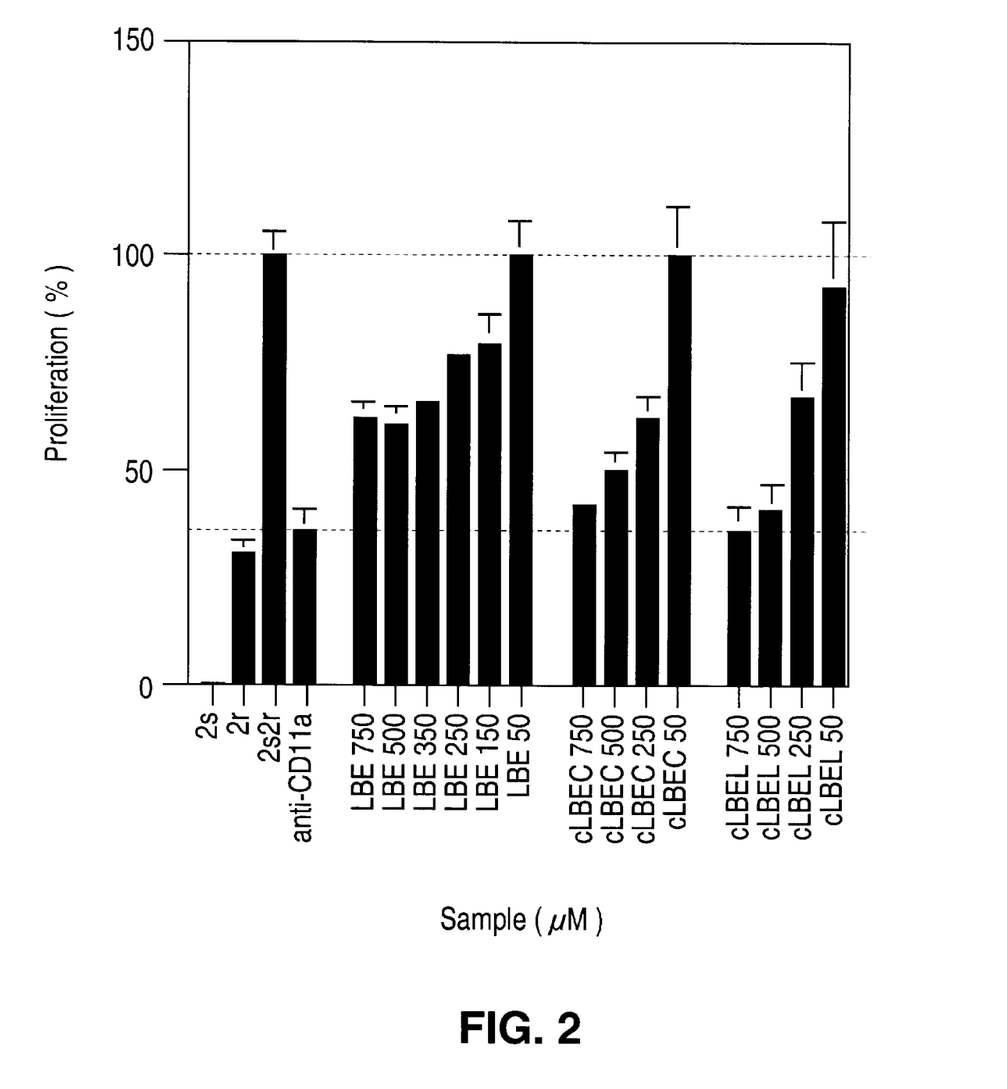
FIG. 2 is a bar graph illustrating the proliferation of responder cells in a mixed lymphocyte reaction assay, and the inhibitory effect of anti-human CD11$a$ antibody, D-LBE (SEQ ID NO:1), cLBEC (SEQ ID NO:2), cLBEL (SEQ ID NO:3) in accordance with the invention on such proliferation.
Figure 3:
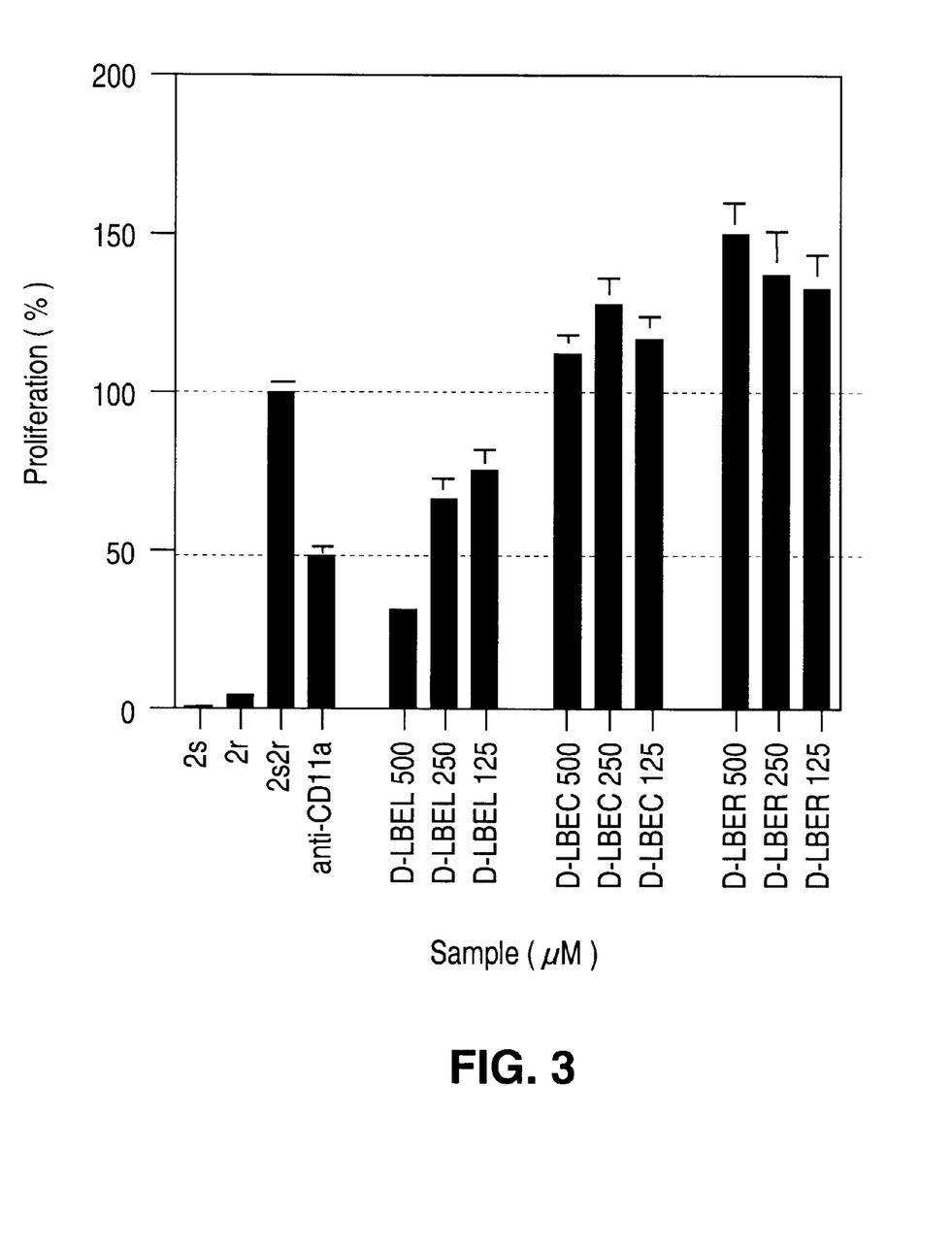
FIG. 3 is a bar graph illustrating the proliferation of responder cells in a mixed lymphocyte reaction assay, and the inhibitory effect of anti-human CD11$a$ antibody, D-LBER (SEQ ID NO:4), D-LBEC (SEQ ID NO:5) and D-LBEL (SEQ ID NO:6) in accordance with the invention on such proliferation.

In FIGS. 2 and 3, the Y-axis values are mean percentage ±SE of proliferation of responders. "2s" refers to irradiated buffy coat cells, and "2r" refers to T-lymphocytes derived from tonsil. "2s2r" refers to non-treated, mixed lymphocyte sample, which is the positive control (represented by dashed line). Inhibition of proliferation by anti-CD11a antibody (Pharmingen, anti-human CD11a) was used as a control for inhibition of the LFA-1/ICAM-1 interaction. These polypeptides are derived from the human LFA-1 β (CD18) subunit.

TABLE 2

Inhibition of T-cell Proliferation Using Peptides at 500 µM

| Antibody/ Peptide (*1) | Inhibition of T-cell Proliferation (%) | Antibody/ Peptide (*2) | Inhibition of T-cell Proliferation (%) | Antibody/ Peptide (*3) | Inhibition of T-cell Proliferation (%) |
|---|---|---|---|---|---|
| Anti-human CD11a | 38.9/5.9 | Anti-human CD11a | 62.0 | Anti-human CD11a | 60.0 |
| IBL | 11.7/N.D. | cIBL | 33.8 | D-IBL | −79.1(*4) |
| IBC | 16.9/N.D. | cIBC | N.D. | D-IBC | −60.3(*4) |
| IBR | 15.0/N.D. | cIBR | 27.0 | D-IBR | −68.7(*4) |
| IEL | N.D./−11.6(*4) | cIEL | 48.8 | D-IEL | −85.2(*4) |
| IEC | N.D./N.D. | cIEC | 23.6 | D-IEC | −9.2(*4) |
| IER | N.D./N.D. | cIER | 19.2 | D-IER | −49.7(*4) |
| LABL | 20.2/N.D. | cLABL | 2.5 | D-LABL | −18.0(*4) |
| LABC | 6.3/N.D. | cLABC | N.D. | D-LABC | −2.24(*4) |
| LABR | 22.5/N.D. | cLABR | N.D. | D-LABR | −94.4(*4) |
| LBEL | N.D./24.8 | cLBEL | 18.0 | D-LBEL | 56.5 |
| LBEC | N.D./N.D. | cLBEC | 18.0 | D-LBEC | −47.6(*4) |
| LBER | N.D./N.D. | cLBER | N.D. | D-LBER | −90.5(*4) |

*1: linear L-peptides
*2: Cyclic L-peptide
*3: Linear D-peptides
*4: minus value indicate that the peptides activated T-lymphocytes.

The one-way MLR has been previously described (Kruisbeek et al., Current Protocols in Immunology, Proliferative Assays for T-Cell Function, '3.12.1–3.12.14 (1991), which is incorporated herein by reference). Specifically, human tonsil T cells were suspended at a concentration of 2–4×106 cells/ml in cell culture medium (RPMI), for use as responders. Stimulator cells were human mononuclear cells isolated from first Ficoll separation of peripheral blood (buffy coat) and were suspended at a concentration of 2–4×106 cells/ml in cell culture medium (RPMI). The stimulator cells were inactivated before use by treatment The sequences of polypeptides tested in this experiment are provided in Table 1.

Referring now to FIG. 2, the MLR assay was performed in the presence of LBE polypeptide (SEQ ID NO:1) of cyclic fragments of LBE, namely cLBEC (SEQ ID NO:2) and cLBEL (SEQ ID NO:3). Each single polypeptide was tested at 50, 150, 250, 350, 500 and 750 µM. At the highest concentration of LBE, the responder T-cell proliferation was inhibited by 30%. On the other hand, the cyclic fragments of LBE were more effective than LBE.

As shown in FIG. 3, MLR was performed in the presence of D-form polypeptide synthesized using D-amino acids, namely D-LBER (SEQ ID NO:4), D-LBEC (SEQ ID NO:5) and D-LBEL (SEQ ID NO:6) at 125, 250, and 500 µM. D-form LBEC (C-LBEC) SEQ ID NO:4) lost the biological function to inhibit T-cell proliferation. As expected, D-LBEC (SEQ ID NO:5) did not show any inhibitory effects in the experiments. IN contrast the D-form polypeptide of LBEL, namely D-LBEL (SEQ ID NO:6) showed an amazing inhibitory effect, which was much more effective than either LBE or cLBEL.

In general D-amino acids are more stable and less immunogenic than polypeptides consisting of natural L-amino acids in biological conditions. The data suggests that the D-form polypeptide (D-LBEL) is one of the best candidate polypeptides to be used in inhibiting ICAM-1/LFA-1 interactions. Furthermore, the polypeptide can be used for the treatment of diseases caused by undesirable ICAM-1/LFA-1 interactions, which include autoimmune disease such as rheumatoid arthritis, multiple sclerosis, allergy, rejection of transplanted organs, and others known to those of the art, by establishing immune tolerance.

A number of embodiments of the present invention have been described. Nevertheless, it will be understood that various modifications may be made without departing from the spirit and scope of the invention. Accordingly, other embodiments are within the scope of the following claims.

What is claimed is:

1. A polypeptide that inhibits the interaction between LFA-1 and ICAM-1 consisting of a sequence as set forth in SEQ ID NO:6.

2. A composition comprising, a polypeptide derived from an LFA-1 binding site that inhibits the interaction between LFA-1 and ICAM-1, wherein the polypeptide has a sequence consisting of a sequence as set forth in SEQ ID NO:6.

3. The composition of claim 2, further comprising a pharmaceutically acceptable carrier.

4. A polypeptide that inhibits the interaction between LFA-1 and ICAM-1 consisting of a sequence as set forth in DLSYSLDDLR, wherein one or more of the amino acids are D-amino acids.

5. A composition comprising a polypeptide derived from an LFA-1 binding site that inhibits the interaction between LFA-1 and ICAM-1, wherein the polypeptide has a sequence consisting of a sequence as set forth in DLSYSLDDLR, and wherein one or more of the amino acids are D-amino acids.

* * * * *